(12) United States Patent
Worthey et al.

(10) Patent No.: US 8,718,950 B2
(45) Date of Patent: May 6, 2014

(54) METHODS AND APPARATUS FOR IDENTIFICATION OF DISEASE ASSOCIATED MUTATIONS

(75) Inventors: Elizabeth Anabel Worthey, Germantown, WI (US); David Paul Dimmock, Brookfield, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 143 days.

(21) Appl. No.: 13/179,151

(22) Filed: Jul. 8, 2011

(65) Prior Publication Data
US 2013/0013213 A1    Jan. 10, 2013

(51) Int. Cl.
| G06F 19/00 | (2011.01) |
| G11C 17/00 | (2006.01) |
| G06F 7/00  | (2006.01) |
| C12Q 1/68  | (2006.01) |

(52) U.S. Cl.
USPC .............. 702/20; 365/94; 707/728; 707/776; 435/6.11

(58) Field of Classification Search
None
See application file for complete search history.

(56) References Cited

U.S. PATENT DOCUMENTS

| 6,955,883 B2 | 10/2005 | Margus et al. |
| 7,584,058 B2 | 9/2009 | Zabeau et al. |
| 7,593,818 B2 | 9/2009 | Zabeau et al. |
| 2003/0157488 A1 | 8/2003 | Cox et al. |
| 2003/0186244 A1 | 10/2003 | Margus et al. |
| 2004/0091890 A1 | 5/2004 | Margus et al. |
| 2004/0101876 A1 | 5/2004 | Mintz et al. |
| 2004/0142325 A1 | 7/2004 | Mintz et al. |
| 2004/0267458 A1 | 12/2004 | Judson et al. |
| 2005/0191731 A1 | 9/2005 | Judson et al. |
| 2006/0286566 A1 | 12/2006 | Lapidus et al. |
| 2009/0104601 A1 | 4/2009 | Zabeau et al. |

FOREIGN PATENT DOCUMENTS

| WO | WO 01/01218 | 1/2001 |
| WO | WO 02/48387 | 6/2002 |
| WO | WO 03/083442 | 10/2003 |
| WO | WO 2004/061616 | 7/2004 |
| WO | WO 2007/148997 | 12/2007 |
| WO | WO 2008/067551 | 6/2008 |
| WO | WO 2008/132763 | 11/2008 |
| WO | WO 2008/152656 | 12/2008 |
| WO | WO 2009/059317 | 5/2009 |
| WO | WO 2009/117122 | 9/2009 |
| WO | WO 2009/146460 | 12/2009 |
| WO | WO 2009/152406 | 12/2009 |
| WO | WO 2010/018600 | 2/2010 |
| WO | WO 2010/018601 | 2/2010 |
| WO | WO 2010/019550 | 2/2010 |
| WO | WO 2010/061407 | 6/2010 |
| WO | WO 2010/073266 | 7/2010 |
| WO | WO 2010/103292 | 9/2010 |
| WO | WO 2011/004405 | 1/2011 |

OTHER PUBLICATIONS

Denny et al. PheWAS: demonstrating the feasibility of a phenome-wide scan to discover gene-disease associations. Bioinformatics vol. 26, pp. 1205-1210 (2010).*
Golden Helix, SVS 7 | Genetic Association Software, retrieved from the Internet on Jun. 22, 2011, http://www.goldenhelix.com/SNP_Variation/index.html.
Golden Helix, Next-Generation Sequencing (NGS) Analysis, 2 pgs., retrieved from the Internet on Jun. 22, 2011, http://www.goldenhelix.com/SNP_Variation/solutions/ngs/index.html.
Helix Tree—SNP Analysis, SNP Analysis Software, 2 pgs., retrieved from the Internet on Oct. 20, 2011, http://www.goldenhelix.com/SNP_Variation/HelixTree/index.html.
SVA Project, retrieved from the Internet on Jun. 30, 3011, http://people.chgv.lsrc.duke.edu/~dg48/sva/intro.php.
SeattleSeq Annotation, retrieved from the Internet on Jun. 30, 2011, http://gvs.gs.washington.edu/SeattleSeqAnnotation/HelpAbout.jsp.
Computational software provides rapid identification of disease-causing gene variations, Jun. 23, 2011, http://www.eurekalert.org/pub_releases/2011-06/uouh-csp061711.php.
CLC Genomics Workbench, Features & Benefits, retrieved from the Internet on Jun. 30, 2011, www.clcbio.com.
Omicia Readies Technology to Interpret Human Genomes for Clinical Projects | In Sequence | Sequencing | GenomeWeb, 3 pgs., Jul. 13, 2010, http://www.genomeweb.com/sequencing/omicia-readies-technology-interpret-human-genomes-clinical-projects.html.
Wang et al., "ANNOVAR: functional annotation of genetic variants from high-throughput sequencing data," Nucleic Acids Research, 2010, vol. 38, No. 16, 7 pgs.
Adzhubei et al., "A method and server for predicting damaging missense mutations," Nature Methods, vol. 7, No. 4, Apr. 2010, 2 pgs.

* cited by examiner

Primary Examiner — John S Brusca
(74) Attorney, Agent, or Firm — Cooley LLP

(57) ABSTRACT

In some embodiments, a non-transitory processor-readable medium includes code to cause a processor to receive a set of variants identified by a comparison of a test DNA sequence with a reference DNA sequence and associate at least one of the set of variants with at least one of a set of annotations each indicative of at least one criterion. The code includes code to cause the processor to filter, based on the set of annotations, the set of variants to identify a subset of variants from the set of variants. Each variant from the subset of variants is associated with at least one common annotation from the set of annotations. The code further includes code to cause the processor to present the subset of variants such that the subset of variants can be used to render a clinical diagnosis.

46 Claims, 9 Drawing Sheets

| Number of Genes: 38 | | |
|---|---|---|
| ID ▲ | Genic ▲ | Premature Stop Codon ▲ |
| AMPD1 | 3 | 1 |
| ANKDD1B | 1 | 1 |
| ARFGEF2 | 5 | 1 |
| CARD8 | 5 | 1 |
| CLCA3P | 3 | 1 |

METHODS AND APPARATUS FOR IDENTIFICATION OF DISEASE ASSOCIATED MUTATIONS

BACKGROUND

While the costs associated with genomic sequencing have dropped dramatically over the last several years, the costs and labor associated with data analysis have remained relatively constant. Thus, there is a great need for tools to support clinical genetics and enable the analysis of an individual's genomic data, for example, in identifying genetic variations potentially associated with a disease phenotype.

SUMMARY

In some embodiments, a non-transitory processor-readable medium includes code to cause a processor to receive a set of genetic variants identified by a comparison of an experimental sample DNA sequence with a reference DNA sequence and associate at least one of the set of variants with at least one of a set of functional or genomic annotations each indicative of at least one criterion. The code includes code to cause the processor to filter, based on the set of annotations, the set of variants to identify a subset of variants from the set of variants. Each variant from the subset of variants is associated with at least one common annotation from the set of annotations. The code further includes code to cause the processor to present the subset of variants such that the subset of variants can be used to render a clinical diagnosis.

BRIEF DESCRIPTION OF THE DRAWINGS

FIG. 5 is an illustration of a user interface associated with filtering variants, according to an embodiment.

FIG. 6 is an illustration of a user interface associated with a detailed view of a gene and variant, according to an embodiment.

FIGS. 7A and 7B illustrate a user interface that displays a detailed view of cross sample variant filtering, according to an embodiment.

DETAILED DESCRIPTION

Figure 1:
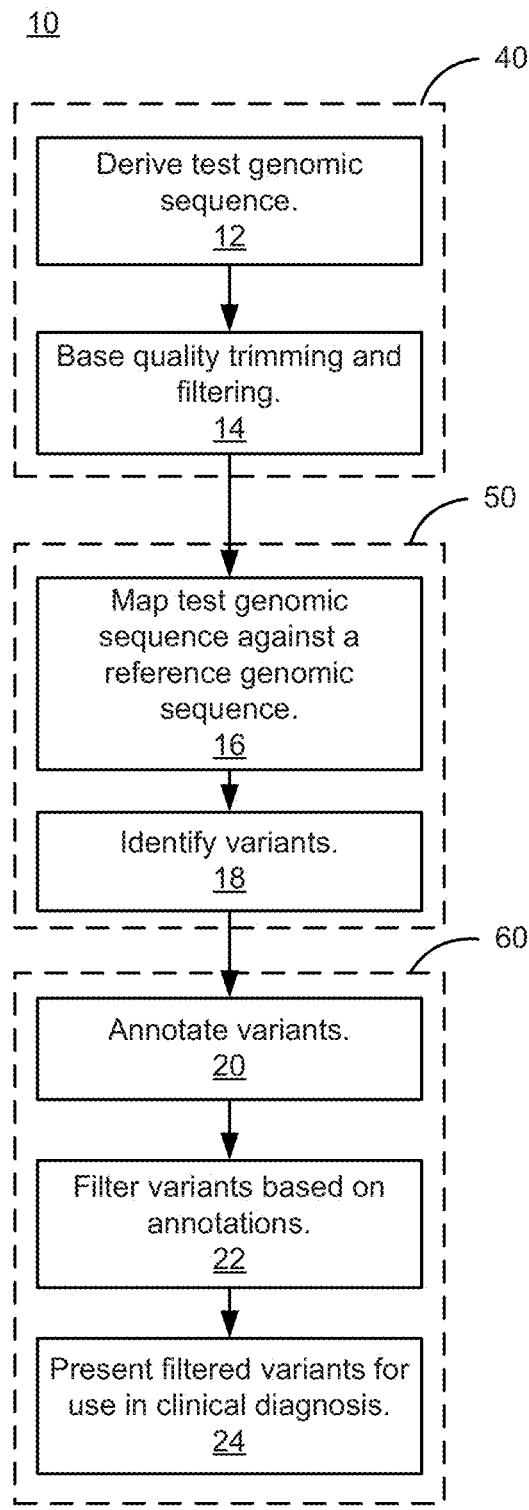
FIG. 1 is a flow chart illustrating a sequencing analysis method, according to an embodiment.

The invention provides methods for analysis of DNA sequence data and associated software and computer systems. The method, which is generally computer implemented, enables a clinical geneticist or other healthcare technician to sift through vast amounts of DNA sequence data, to identify potential disease-causing genomic variants. In some cases, the DNA sequence data is from a patient who may be suspected of having a genetic disorder.

Therefore, in one aspect, the invention provides a method for identifying a genetic disorder in an individual, or identifying a genetic variant that is causative of a phenotype in an individual. The method comprises determining a DNA sequence for a patient suspected of having a genetic disorder, identifying sequence variants, annotating the identified variants based on one or more criteria, and filtering or searching the variants at least partially based on the annotations, to thereby identify potential disease-causing variants.

In some embodiments, the sequence is obtained by use of a sequencing instrument, or alternatively, DNA sequence data is obtained from another source, such as for example, a commercial sequencing service provider. The term "DNA sequence" as used herein refers not only to chromosomal sequence, but also to cDNA sequence, or any nucleotide sequence information that allows for detection of genetic disease. Generally, the amount of sequence information is such that computational tools are required for data analysis. For example, the sequence data may represent at least half of the individual's genomic or cDNA sequence (e.g., of a representative cell population or tissue), or the individuals entire genomic or cDNA sequence. In various embodiments, the sequence data comprises the nucleotide sequence for at least 1 million base pairs, at least 10 million base pairs, or at least 50 million base pairs. In certain embodiments, the DNA sequence is the individual's exome sequence or full exonic sequence component (i.e., the exome; sequence for each of the exons in each of the known genes in the entire genome). Further, the source of genomic DNA or cDNA may be any suitable source, and may be a sample particularly indicative of a disease or phenotype of interest, including blood cells (e.g, PBMCs, or a T-cell or B-cell population). In certain embodiments, the source of the sample is a tissue or sample that is potentially malignant.

As used herein, "whole genome sequence" includes the entire sequence (including all chromosomes) of an individual's germline genome. In some embodiments, the concatenated length for a whole genome sequence is approximately 3.2 Gbases or 3.2 billion nucleotides.

The DNA sequence may be determined by any suitable method. For example, the DNA sequence may be a cDNA sequence determined by clonal amplification (e.g., emulsion PCR) and sequencing. Base calling may be conducted based on any available method, including Sanger sequencing (chain termination), pH sequencing, pyrosequencing, sequencing-by-hybridization, sequencing-by-ligation, etc. The sequencing output data may be subject to quality controls, including filtering for quality (e.g., confidence) of base reads. Exemplary sequencing systems include 454 pyrosequencing (454 Life Sciences), Illumina (Solexa) sequencing, SOLiD (Applied Biosystems), and Ion Torrent Systems' pH sequencing system.

The DNA sequence is mapped with one or more reference sequences to identify sequence variants. For example, the base reads are mapped against a reference sequence, which in various embodiments is presumed to be a "normal" non-disease sequence. The DNS sequence derived from the Human Genome Project is generally used as a "premier" reference sequence. A number of mapping applications are known, and include GSMAPPER, ELAND, MOSAIK, and MAQ. Various other alignment tools are known, and could also be implemented to map the base reads.

Based on the sequence alignments, and mapping results, sequence variants are identified. Types of variants include insertions, deletions, indels (a colocalized insertion and deletion), translocations, inversions, and substitutions. While the type of variants analyzed are not limited, the most numerous of the variant types will be single nucleotide substitutions, for which a wealth of data is currently available. In various embodiments, comparison of the test sequence with the reference sequence will produce at least 500 variants, at least 1000 variants, at least 3,000 variants, at least 5,000 variants, at least 10,000 variants, but in some embodiments, will produce at least 1 million variants, at least three million variants, or at least 10 million variants. The tools provided herein enable the user to navigate the vast amounts of genetic data to identify potentially disease-causing variants.

A wealth of data is extracted for the identified variants, including one or more of conservation scores, genic/genomic location, zygosity, SNP ID, Polyphen and SIFT predictions, splice site predictions, amino acid properties, disease associations, annotations for known variants, variant or allele frequency data, and gene annotations. Data may be calculated and/or extracted from one or more internal or external databases. Since certain categories of annotations (e.g., amino acid properties/PolyPhen and SIFT data) are dependent on a nature of the region of the genome in which they are contained (e.g., whether a variant is contained within a region translated to give rise to an amino acid sequence in a resultant protein), these annotations can be carried out for each known transcript. Exemplary external databases include OMIM (Online Mendelian Inheritance in Man), HGMD (The Human Gene Mutation Databse), PubMed, PolyPhen, SIFT, SpliceSite, reference genome databases, the University of California Santa Cruz (UCSC) genome database, the BioBase biological databases, the dbSNP Short Genetic Variations database, the Rat Genome Database (RGD), and/or the like. Various other databases may be employed for extracting data on identified variants. Variant information may be further stored in a central data repository, and the data extracted for future sequence analyses.

Based on extracted information, the variants are annotated to facilitate filtering of the variants, such that the variants meeting certain criteria can be easily identified. In some embodiments, variants are interpreted as being benign, pathogenic, or variants of unknown significance, based upon available information including for example, information from human mutational databases, and data stored in a central repository. In some embodiments, the variants are annotated as meeting, for example, one or more of the following criteria:
   (i) the variant is reported to cause a disorder and recognized to cause a disorder,
   (ii) the variant is unreported but would be expected to cause a disorder,
   (iii) the variant is unreported and of the type that might be causative of a disorder,
   (iv) the variant is unreported and unlikely to cause a disorder,
   (v) the variant is reported and is a recognized neutral variant, and/or
   (vi) the variant is unknown or not expected to be causative of disease, but is associated with clinical presentation.

Alternative or additional bases for annotation may be employed, as long as the annotations essentially categorize variants as having a known association with disease, having a known neutral effect, or having an unknown effect. For variants having an unknown effect, various sub-categories are usually preferred to identify or score variants based on a predicted biological impact. In various embodiments, the annotations are assigned to sequence variants on the basis of a change in encoded amino acid, a change in an RNA processing site, or information from a human gene mutational database. For example, the variants may lead to a change in the encoded amino acid at one or more positions (a non-conservative substitution), and thus the annotation may take into account the damage prediction as a result of such amino acid change to determine whether a resulting phenotype change (and a resulting disorder) is likely. In some embodiments, annotations can be produced for all known transcripts. Annotations may be conducted automatically, as described in detail below, or conducted by independent examination, or both.

Once variants have been annotated, the variants can be filtered, based on the annotations, in response to user queries to identify potential disease causing variants, and/or to confirm or rule out the presence of a genetic disorder. Alternatively, one can browse variants according to other criteria of interest, including browsing or searching for variants in one or more genes of interest or a genetic locus of interest, or browsing or searching for variants with predicted biological impact, which may be based on polypeptide damage predictions, splice site predictions, known gene-disease associations, or matching with variants stored in a central data repository with patient phenotype information, or variant frequency. As described in detail herein, the invention in certain aspects provides a user interface to enable such filtering and searching.

Variants may be tagged by the user with additional descriptive information to aid subsequent analysis. For example, confidence in the existence of the variant can be recorded as confirmed, preliminary, or sequence artifact. Certain sequencing technologies have a tendency to produce certain types of sequence artifacts, and the invention allows such suspected artifacts to be recorded. The variants may be further tagged in basic categories of benign, pathogenic, or unknown, or as potentially of interest.

The method may employ a computer-readable medium, or "non-transitory processor-readable medium."

In particular, queries can be run to identify variants meeting certain criteria, or variant report pages can be browsed by chromosomal position or by gene, the latter allowing researchers to focus on only those variations that exist in a particular set of genes of interest. In some embodiments, the user selects only variants with well-documented and published disease associations (e.g., by filtering based on HGMD or other disease annotation). Alternatively, the user can filter for variants not previously associated with disease, but of a type likely to be deleterious, such as those introducing frameshifts, non-synonymous substitutions (predicted by Polyphen or SIFT), or premature terminations. Further, the user can exclude from analysis those variants believed to be neutral (based on their frequency of occurrence in studies populations), for example, through exclusion of variants in dbSNP. Additional exclusion criteria include mode of inheritance (e.g., heterozygosity), depth of coverage, and quality score.

In certain embodiments, base calling is carried out to extract the sequence of the sequencing reads from an image file produced by an instrument scanner. Following base calling and base quality trimming/filtering, the reads are mapped against a reference sequence (assumed to be normal for the phenotype under analysis) to identify variations (variants) between the two with the assumption that one or more of these differences will be associated with phenotype of the individual whose DNA is under analysis. Subsequently, each variant is annotated with data that can be used to determine the likelihood that that particular variant is associated with the phenotype under analysis. The analysis may be fully or partially automated as described in detail below, and may include use of a central repository for data storage and analysis, and to present the data to analysts and clinical geneticists in a format that makes identification of variants with a high likelihood of being associated with the phenotypic difference more efficient and effective.

In some embodiments, a user is been provided with the ability to run cross sample queries where the variants from multiple samples are interrogated simultaneously. In such embodiments, for example, a user can build a query to return data on only those variants that are exactly shared across a user defined group of samples. This can be useful for family based analyses where the same variant is believed to be associated with disease in each of the affected family members. For another example, the user can also build a query to return only those variants that are present in genes where the gene contains at least one, but not necessarily the same, variant. This can be useful where a group of individuals with disease are not related (the variants associated with the disease are not necessary exactly the same, but result in a common alteration in normal function). For yet another example, the user can specify to ignore genes containing variants in a user defined group of samples. This can be useful to exclude polymorphisms (variants believed or confirmed not to be associated with disease) where the user has access to a user defined group of control individuals who are believed to not have the disease associated variant. For each of these queries a user can additionally filter the variants by specifying any or all of the previously discussed filters (using the advanced search shown, for example, in FIG. 5) on top of the cross sample analyses. This allows a user to identify variants matching these criteria, which are shared between or segregated amongst samples.

FIG. 1 is a flow chart illustrating a sequencing analysis method 10. The sequencing analysis method 10 includes a primary analysis phase 40, a secondary analysis phase 50 and a tertiary analysis phase 60. As shown in FIG. 1, the primary analysis phase 40 includes deriving a test DNA sequence associated with an individual, at 12. In some embodiments, for example, an instrument scanner can produce an image file associated with the individual's DNA sequence. Base calling can then be performed to extract the test DNA sequence from the image file. Base quality trimming and filtering can then be performed on the test DNA sequence, at 14.

The secondary analysis phase 50 includes mapping the test DNA sequence against a reference DNA sequence, at 16, and identifying variations and/or differences (variants) between the test DNA sequence and the reference DNA sequence, at 18. In some embodiments, the reference DNA sequence can be deemed "normal" and/or "a baseline" for one or more phenotypes, disorders and/or diseases under analysis. Thus, an assumption can be made that one or more variants between the test DNA sequence and the reference DNA sequence can be associated with the phenotype, disorder and/or disease under analysis. In some embodiments, the test DNA sequence and/or the reference DNA sequence is an entire human genome. In other embodiments, the test DNA sequence and/or the reference DNA sequence includes between 1 million base pairs and 50 million base pairs. In still other embodiments, the test DNA sequence and/or the reference DNA sequence includes fewer than 1 million base pairs or greater than 50 million base pairs.

In some embodiments, any suitable application, tool and/or system can be used to perform the primary analysis phase 40 and/or the secondary analysis phase 50. In some embodiments, for example, a tool such as Roche's GSMAPPER, ELAND, SourceForge.net's MAQ (Mapping and Assembling with Qualities), Boston College's MOSAIK and/or the like can be used to perform the primary analysis phase 40 and/or the secondary analysis phase 50. These tools can output a result that includes the identified variants that can be input into a variant analysis system that implements the tertiary analysis phase 60. Different tools can output the results of the secondary analysis phase 50 in different file formats and/or syntaxes. As such, the variant analysis system can be configured to receive various file formats and/or syntaxes of variant data and convert the various file formats and/or syntaxes of variant data into a common file format or syntax prior to performing the tertiary analysis phase 60.

The tertiary analysis phase 60 includes annotating the variants, at 20. Specifically, each variant can be annotated with data that can be used to determine a likelihood that that particular variant is associated with the phenotype, disorder and/or disease under analysis. A variant can be annotated, for example, with functional information, amino acid properties, conservation scores, zygosity data, allele frequencies, quality scores, disease associations, PolyPhen damage predictions, a change in an RNA processing site, splice site predictions, or other information from a human gene mutational database. Additionally, in some embodiments, each variant can be annotated with data that indicates whether (1) the variant has been reported to cause a disorder and recognized to cause a disorder; (2) the variant is unreported but expected to cause a disorder; (3) the variant is unreported and of the type that might be causative of a disorder; (4) the variant is unreported and unlikely to cause a disorder; (5) the variant has been reported and is a recognized neutral variant; and/or (6) the variant is unknown or not expected to be causative of disease but has a known association with clinical presentation. Such annotations are extracted from existing datasets and/or calculated using the variant analysis system.

The variants can then be filtered based on these annotations, at 22 and the filtered variants can be presented to a user (e.g., a clinical geneticist) for use in a clinical diagnosis, at 24. For example, a user can filter the variants using the annotations such that variants meeting a specific criteria are presented. The user can then use these variants in connection with rendering a clinical diagnosis.

Figure 2:
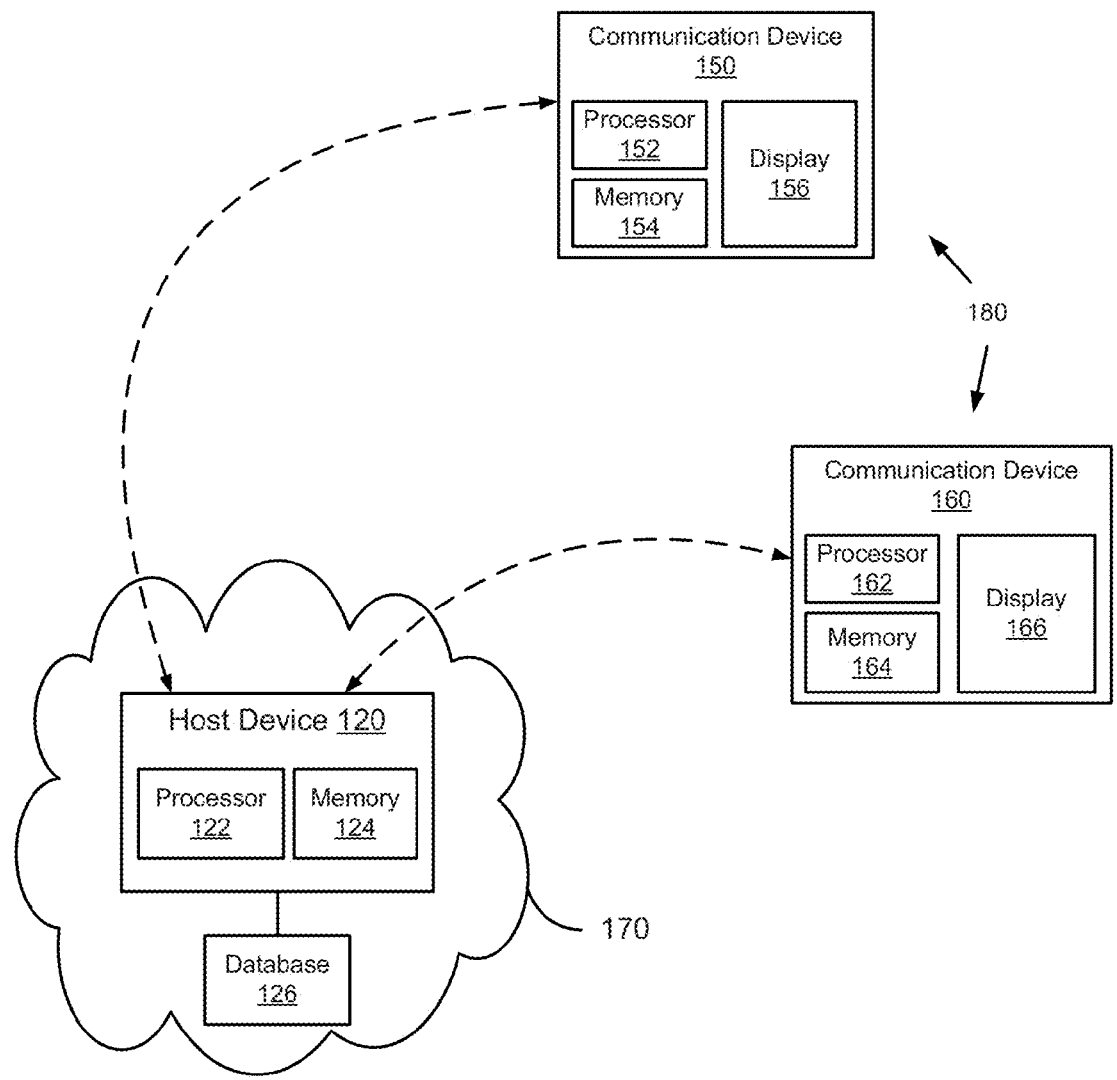
FIG. 2 is a schematic diagram that illustrates communication devices in communication with a host device via a network, according to an embodiment.

FIG. 2 is a schematic diagram that illustrates communication devices 180 in communication with a host device 120 via a network 170 to implement a variant analysis system, according to an embodiment. Specifically, communication device 150 is configured to communicate with the host device 120. Similarly, communication device 160 is configured to communicate with the host device 120. The network 170 can be any type of network (e.g., a local area network (LAN), a wide area network (WAN), a virtual network, a telecommunications network, the Internet) implemented as a wired network and/or wireless network. As described in further detail herein, in some embodiments, for example, the communication devices 180 are personal computers connected to the host device 120 via an internet service provider (ISP) and the Internet (e.g., network 170).

The host device 120 can be any type of device configured to send data over the network 170 to and/or receive data from one or more of the communication devices 180. In some embodiments, the host device 120 can be configured to function as, for example, a server device (e.g., a web server device), a network management device, and/or so forth.

The host device 120 includes a memory 124 and a processor 122. The memory 124 can be, for example, a random access memory (RAM), a memory buffer, a hard drive, and/or so forth. In some embodiments, the memory 124 of the host device 120 includes data used to facilitate a variant analysis system. In such embodiments, for example, the host device 120 is configured to execute code that implements the variant analysis system. As such, the host device 120 can send data associated with the variant analysis system to and receive data associated with the variant analysis system from the communication devices 180. For example, as described in further detail herein, the host device 120 can send data associated with a result of a variant analysis to the communication devices 180. Additionally, the host device 120 can receive data associated with a variant filtering request from a communication device 180. In some embodiments, the host device 120 can receive data from the communication devices 180 pertaining to variant analysis. For example, the host device can receive an indication that a user of a communication device 180 wishes to import variant data, a user of a communication device 180 wishes to annotate variant data, a user of a communication device 180 wishes to filter variant data, and/or the like.

In some embodiments, the memory 124 of the host device 120 stores account information associated with users of the variant analysis system. In such embodiments, for example, the host device 120 can store a username and password associated with a user, preferences associated with the user, a listing of variant analyses conducted by the user, and/or the like. In other embodiments, such information is stored in a database (e.g., database 126) operatively coupled to the host device 120.

The database 126 is operatively coupled to the host device 120. In some embodiments, the data associated with the variant analysis (e.g., variant annotation data, variant identification data, data associated with diseases and/or phenotypes, specific variant data imported to the memory 124 by a user of a communication device 180, and/or the like) is stored in the database 126. In such embodiments, the host device 120 can query the database 126 for data associated with the variant analysis. Specifically, when a user wishes to view data associated with a variant analysis, a communication device 180 can send a request for data to the host device 120; the host device 120 can query the database 126 for the requested data; and the host device 120 can send the requested data to the communication device 180.

In some embodiments, for example, the database 126 can be an Oracle 11 g database and/or the like. In some embodiments, the host device 120 can facilitate communication between the communication devices and the database 126 using a middleware layer. In some embodiments, such a middleware layer can be a Java middleware layer and the host device 120 can be a Java application server.

Each of the communication devices 180 can be, for example, a computing entity (e.g., a personal computing device such as a desktop computer, a laptop computer, etc.), a mobile phone, a personal digital assistant (PDA), and/or so forth. Although not shown, in some embodiments, each of the communication devices 180 can include one or more network interface devices (e.g., a network interface card) configured to connect the communication devices 180 to the network 170. In some embodiments, the communication devices 180 can be referred to as client devices.

As shown in FIG. 2, the communication device 160 has a processor 162, a memory 164, and a display 166. The memory 164 can be, for example, a random access memory (RAM), a memory buffer, a hard drive, and/or so forth. The display 166 can be any suitable display, such as, for example, a liquid crystal display (LCD), a cathode ray tube display (CRT) or the like. Similar to communication device 160, the communication device 150 has a processor 152, a memory 154, and a display 156.

In some embodiments, a web browser application can be stored in the memory 164 of the communication device 160. Using the web browser application, the communication device 160 can send data to and receive data from the host device 120. Similarly, the communication device 150 can include a web browser application. In such embodiments, the communication devices 180 act as thin clients. This allows minimal data to be stored on the communication devices 180. In other embodiments, the communication devices 180 can include an application specific to communicating with the host device 120 when using the variant analysis system. In such embodiments, the communication devices 180 can download the application from the host device 120 prior to running the variant analysis system. In some embodiments, such an application can be, for example, an Adobe Flex application executing on the host device 120 using a web browser application.

As discussed above, the communication devices 180 can send data to and receive data from the host device 120 associated with a variant analysis system. In some embodiments, the data sent between the communication devices 180 and the host device 120 can be formatted using any suitable format. In some embodiments, for example, the data can be formatted using extensible markup language (XML), hypertext markup language (HTML) and/or the like.

In some embodiments, one or more portions of the host device 120 and/or one or more portions of the communication devices 180 can include a hardware-based module (e.g., a digital signal processor (DSP), a field programmable gate array (FPGA)) and/or a software-based module (e.g., a module of computer code to be executed at a processor, a set of processor-readable instructions that can be executed at a processor). In some embodiments, one or more of the functions associated with the host device 120 (e.g., the functions associated with the processor 122) can be included in one or more modules (see, e.g., FIG. 3). In some embodiments, one or more of the functions associated with the communication devices 180 (e.g., functions associated with processor 152 or processor 162) can be included in one or more modules. In some embodiments, one or more of the communication devices 180 can be configured to perform one or more functions associated with the host device 120, and vice versa.

Figure 3:
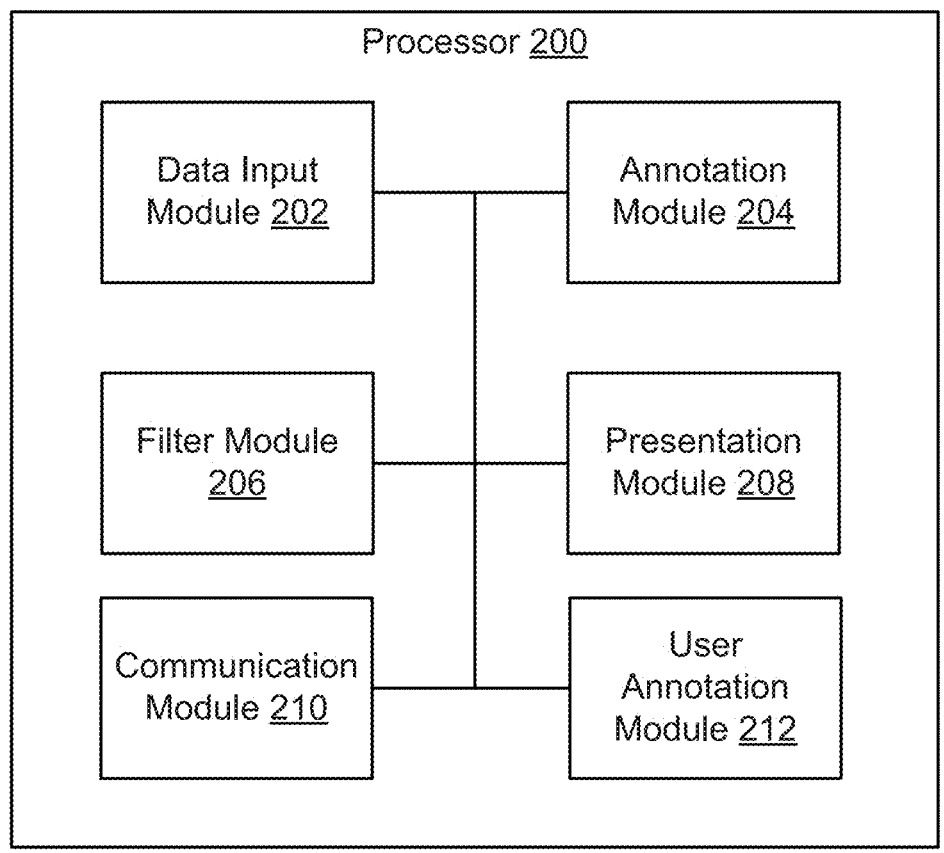
FIG. 3 is a schematic illustration of a processor of a host device, according to an embodiment.

FIG. 3 is a schematic illustration of a processor 200 of a host device (e.g., host device 120 of FIG. 2), according to another embodiment. The processor 200 includes a data input module 202, an annotation module 204, a filter module 206, a presentation module 208, a communication module 210 and a user annotation module 212. Such modules can be configured to implement a variant analysis system for performing a tertiary analysis phase (e.g., tertiary analysis phase 60 of FIG. 1) of a sequencing analysis method (e.g., sequencing analysis method 10 of FIG. 1).

Such modules can be hardware-based modules (e.g., a digital signal processor (DSP), a field programmable gate array (FPGA)) and/or software-based modules (e.g., a module of computer code to be executed at processor 200, a set of processor-readable instructions that can be executed at a processor 200). While each module is shown in FIG. 3 as being in direct communication with every other module, in other embodiments, each module need not be in direct communication with every other module. For example, the data input module 202 might not be in direct communication with the presentation module 210.

The communication module 210 can facilitate communication between the processor 200 of the host device and one or more communication devices (e.g., communication devices 180 of FIG. 2). Accordingly, the other modules of the processor 200 can use the communication module 210 to send data to and receive data from the communication devices. Additionally, in some embodiments, the communication module 210 can facilitate communication between the processor 200 of the host device and one or more databases (e.g., database 126 of FIG. 2). Accordingly, the processor 200 can send data, queries, and/or the like to a database via communication module 210. Similarly, the processor 200 can receive data in response to queries via the communication module 210.

The data input module 202 is configured to receive data from a communication device (e.g., via communication module 210). In some embodiments, such data can include variant data associated with a specific individual, variant annotation data, and/or the like. Variant data can include variations identified by mapping a test DNA sequence against a reference DNA sequence as produced in a secondary analysis phase of a sequencing analysis method, as described above with respect to FIG. 1. In some embodiments, the test DNA sequence and/or the reference DNA sequence is an entire human genome. In other embodiments, the test DNA sequence and/or the reference DNA sequence includes between 1 million base pairs and 50 million base pairs.

Variant annotation data can include information and/or identified relationships used to annotate variants. In some embodiments, the data input module 202 can send the data to a database (e.g., database 126) for storage and future retrieval and/or use. In other embodiments, the input module 202 can send the data to another module (e.g., annotation module 204) for further processing and/or analysis.

As discussed above, in some embodiments, different secondary analysis phase tools output variant data in different file formats and/or syntax. Accordingly, in some embodiments, the data input module 202 can be configured to receive variant data in multiple file formats and/or syntaxes. The data input module 202 can then convert the variant data into a single common format and/or syntax. For example, the data input module 202 can be configured to convert variant data received in a first file format and/or syntax and produced by a first secondary analysis phase tool to a second file format and/or syntax. Similarly, the data input module 202 can be configured to convert variant data received in a third file format and/or syntax and produced by a second secondary analysis phase tool to the same second file format and/or syntax. The remaining portions of the variant analysis system can be configured to read and/or analyze the variant data in the common format and/or syntax.

The annotation module 204 is configured to receive variant data from the data input module 202 and associate the variants associated with the variant data with annotations. For example, each variant can be annotated with data that can be used to determine a likelihood that that particular variant is associated a disease, disorder and/or phenotype under analysis. The annotation module 204 can annotate a variant with, for example, functional information, amino acid properties, conservation scores, zygosity data, allele frequencies, quality scores, disease associations, PolyPhen damage predictions, a change in an RNA processing site, splice site predictions, and/or the like. Additionally, in some embodiments, the annotation module 204 can annotate one or more variants with data that indicates whether (1) the variant has been reported to cause a disorder and recognized to cause a disorder; (2) the variant is unreported but expected to cause a disorder; (3) the variant is unreported and of the type that might be causative of a disorder; (4) the variant is unreported and unlikely to cause a disorder; (5) the variant has been reported and is a recognized neutral variant; and/or (6) the variant is unknown or not expected to causative of disease but has a known association with clinical presentation. In some embodiments, variants can be associated with annotations on the basis of a change in encoded amino acid, a change in an RNA processing site or information from a human gene mutational database. Such annotations are extracted from existing datasets and/or calculated using the variant analysis system.

Figure 4:
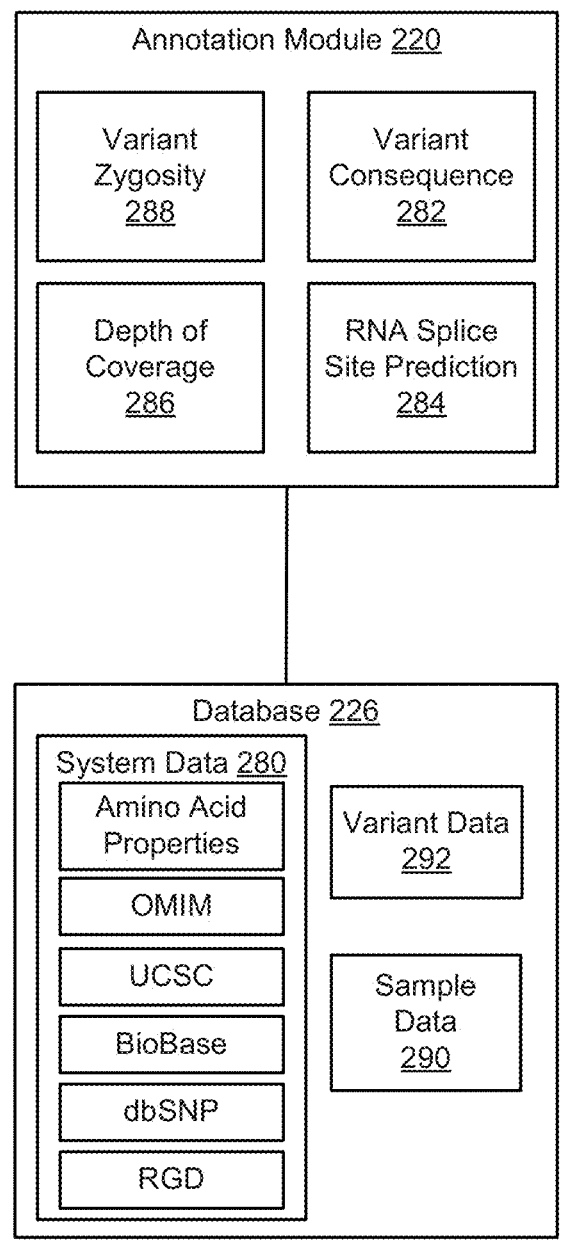
FIG. 4 is a detailed view of an annotation module and a database used in annotating variants, according to an embodiment.

FIG. 4 is a detailed view of an annotation module 220 (similar to annotation module 204 of FIG. 3) and a database 226 (e.g., similar to database 126) for use in annotating variants. In some embodiments, the database 226 stores information used by the annotation module 220 to annotate variants. In such embodiments, the information can be stored in database 226 and retrieved from database 226 by the annotation module during an annotation process. Specifically, the host device 220 can receive system data 280, variant data 292 and/or sample data 290 from the database 226 during an annotation process. Variant data 292 can be associated with the variants identified in a secondary phase analysis and provided to the database 226 by a communication device (e.g., via data input module 202). Sample data 290 can be reference sequence data received from, for example, Illumina, 454 Life Sciences and/or the like. System data 280 can be extracted from one or more internal or external databases such as, for example, an amino acid properties database, OMIM (Online Mendelian Inheritance in Man), HGMD (The Human Gene Mutation Databse), PubMed, PolyPhen, SIFT, SpliceSite, reference genome databases, the University of California Santa Cruz (UCSC) genome database, the BioBase biological databases, the dbSNP Short Genetic Variations database, the Rat Genome Database (RGD), and/or the like. Such system data can be used to annotate the variant data 292.

The annotation module 220 includes functionality to calculate variant consequence 282, RNA splice site predictions 284, depth of coverage 286 and variant zygosity 288. In some embodiments, RNA spice site prediction 284 can be calculated using GeneSplicer, Splice Site and/or any other tool or algorithm. Variant consequence 282 can be calculated using PolyPhen, SIFT, and/or the like.

Returning to FIG. 3, after annotating the variant data, the annotation module 204 can store the variant data and its associated annotations in a database (e.g., database 126 of FIG. 1). This allows a user (e.g., a clinical geneticist) to perform subsequent analysis using the variant data and the annotations.

The filter module 206 is configured to allow users (e.g., clinical geneticists) to filter, search and/or query the variant data for variants having one or more commonalities. Specifically, the filter module 206 can be configured to receive search parameters from a communication device (e.g., via communication module 210). For example, a user might send an instruction to the filter module 206 to search for all variants that are highly conserved, homozygous and novel (i.e., not identified in a reference data set). For another example, a user might send an instruction to the filter module 206 to search for all variants already associated with a disease. Based on the search parameters, the filter module 206 can provide a query to the database (e.g., database 126 of FIG. 1) storing the annotated variant data. The database can identify and return the variants matching the search parameters.

The presentation module 208 is configured to provide a graphical user interface to a user of the variant analysis system. In some embodiments, for example, the presentation module 208 sends instructions to a communications device (e.g., via communications module 210) to render various user interfaces on a display of the communications device. For example, the presentation module 208 can send instructions to cause the communications device to provide a data input user interface, which allows a user to load variant data, on a display of the communications device. For another example, the presentation module can send instructions to cause the communications device to provide a variant filter user interface (e.g., FIG. 4) on a display of the communications device. For yet another example, the presentation module can send instructions to cause the communications device to provide information associated with a specific gene and/or variant (e.g., FIG. 5). A user of the variant analysis system can control and/or use the variant analysis system via the various user interfaces of the variant analysis system.

Figure 5:
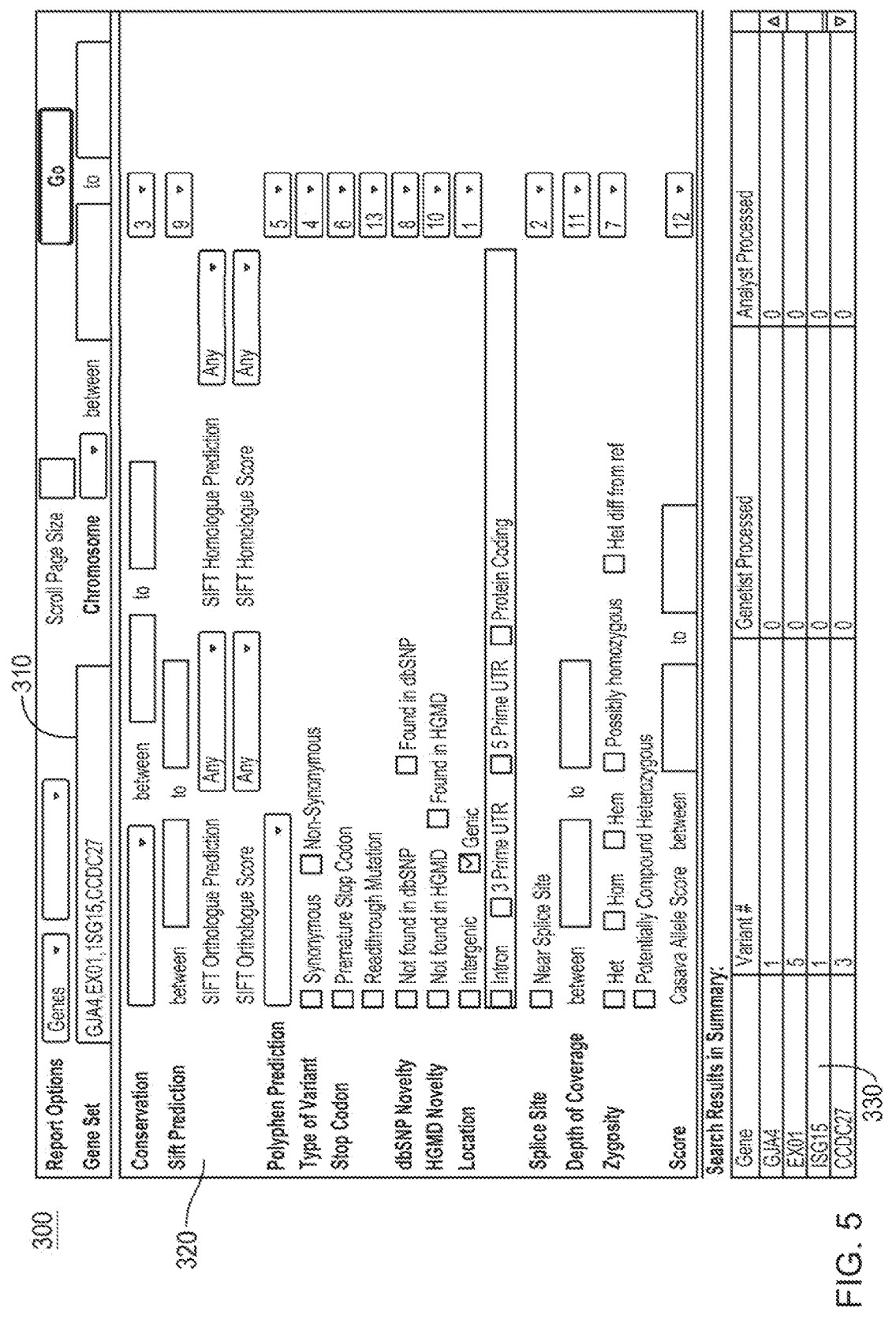

FIG. 5, for example, is an illustration of a user interface 300 associated with filtering variants based on annotations of those variants. User interface 300 can be provided to a communications device by the presentation module 208. The user can then provide search and/or filter parameters and/or criteria to the filter module 206 using user interface 300.

User interface 300 includes a gene search portion 310, an advanced search portion 320 and a search results summary portion 330. The gene search portion 310 of user interface 300 allows a user to search for and/or filter variants by gene identifier and/or gene set identifier. For example, as shown in FIG. 5, a search can be conducted for GJA4,EXO1,ISG15, CCDC27.

The advanced search portion 320 of user interface 300 allows a user to search for and/or filter variants using a variety of parameters such as, for example, conservation, sift prediction, frequency, polyphen prediction, hetrozygosity, splice site, and/or the like. The advanced search portion 320 of user interface 300 also allows a user to search for and/or filter variants that are synonymous, non-synonymous, novel, known-biobase, known-dbSNP, intergenic, genic, protein coding, intronic, 3 prime UTR and/or 5 prime UTR. The search results summary portion 330 includes a summary of the genes identified as variants using the parameters identified in the gene search portion 310 and the advanced search portion 320.

Figure 6:
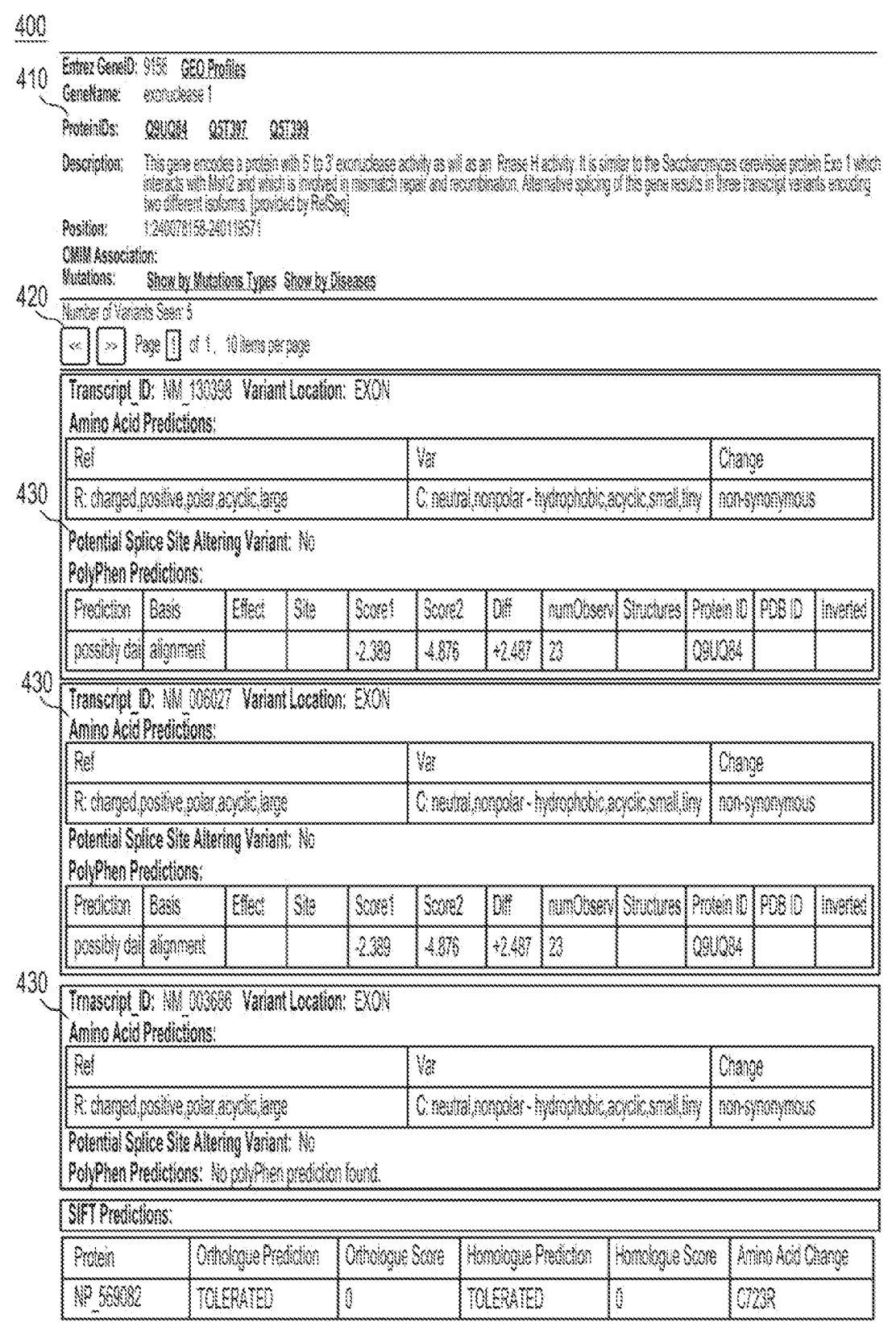

FIG. 6 is an illustration of a user interface 400 that displays a detailed view of a gene and variant identified by filtering the variant data. Similar to user interface 300, user interface 400 can be provided to a communications device by the presentation module 208. The user can then analyze in detail the genes and variants identified by filtering the variant data.

Specifically, user interface 400 includes a gene summary portion 410 and a variant summary portion 420. The gene summary portion 410 provides information associated with a particular gene such as, for example, a description, protein identifiers, position information, and/or the like. The variant summary portion 420 includes information associated with the variants identified for that gene. Additionally, the variant summary portion includes a variant summary for each known transcript 430.

Returning to FIG. 3, the user annotation module 212 can receive annotations made by users of the variant analysis system. Specifically, a user of the variant analysis system can identify the variants as being confirmed, preliminary and/or an artifact. Additionally, a user of the variant analysis system can flag variants as likely to be benign, pathogenic or of unknown significance. Such user annotations can be added to the database (e.g., database 126) such that variants can be automatically annotated with the user provided annotations (e.g., by annotation module 204) during subsequent analysis. This allows users of the system to add their professional analysis to the annotated variants, leading to a clinical diagnosis.

Figure 7A:
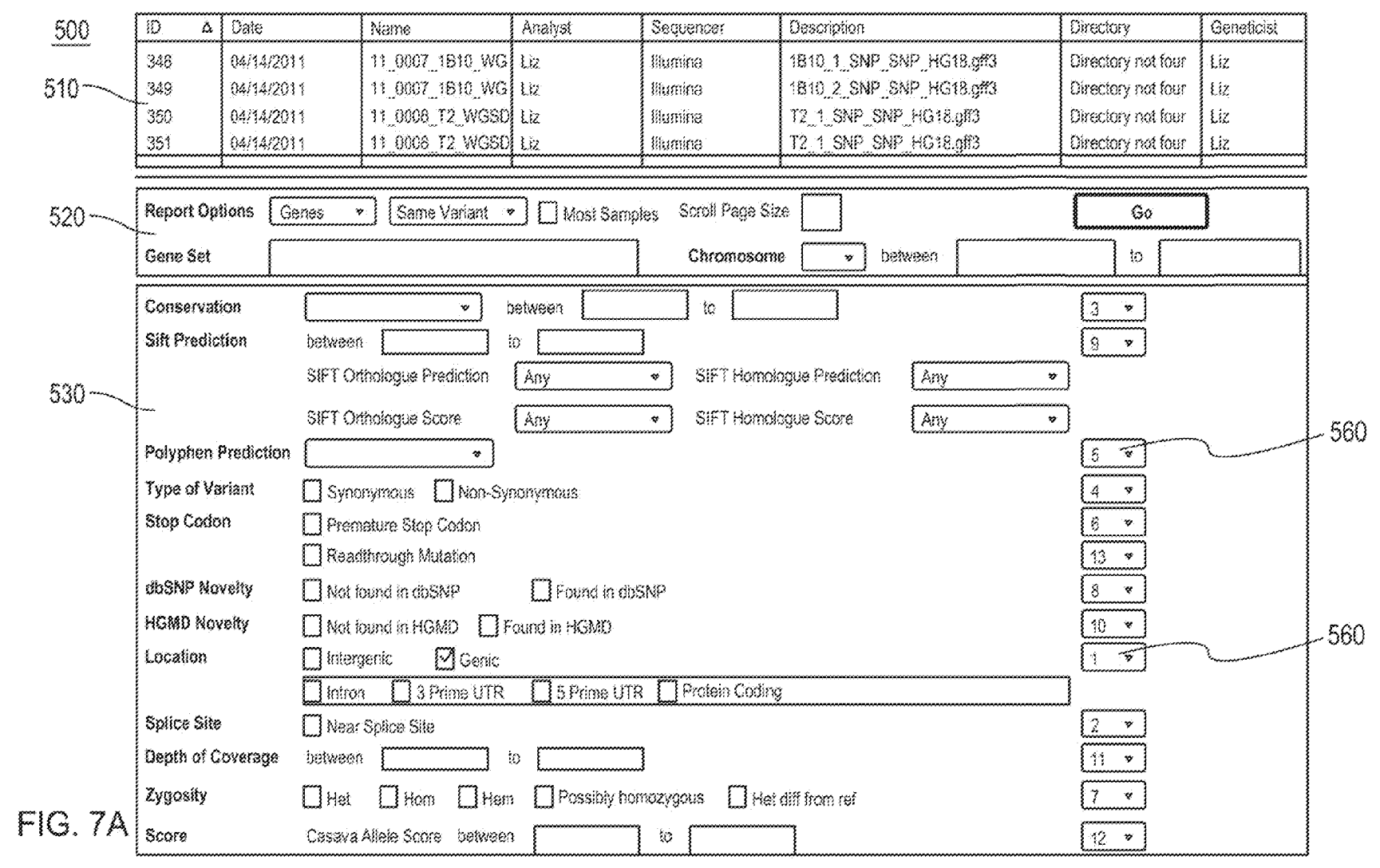

FIGS. 7A and 7B illustrate a user interface 500 that displays a detailed view of cross sample variant filtering. Similar to user interface 300 (shown and described with respect to FIG. 5), user interface 500 can be provided to a communications device by the presentation module 208 (FIG. 3). A user of the communication device can then analyze in detail the genes and/or variants identified by filtering the variant data using sample selection.

Specifically, user interface 500 includes a selection portion 510, a methodology portion 520, an additional filter portion 530 and a results portion 540. The selection portion 510 allows a user to select samples to be analyzed 510. The methodology portion 520 allows a user of the communication device to select a methodology to be used for cross sample analysis. The additional filter portion 530 can be used to further define the methodology selected in the methodology portion 520. The returned cross sample variant containing genes can be presented to the user as a table in the results portion 540. In some embodiments, additional columns 550 of data, based on the variant annotations, can be added to the table in the results portion 540. A user can select an order in which the data appears in the table of the results portion 540 (e.g., an order of the columns) using selection inputs 560.

Figure 8:
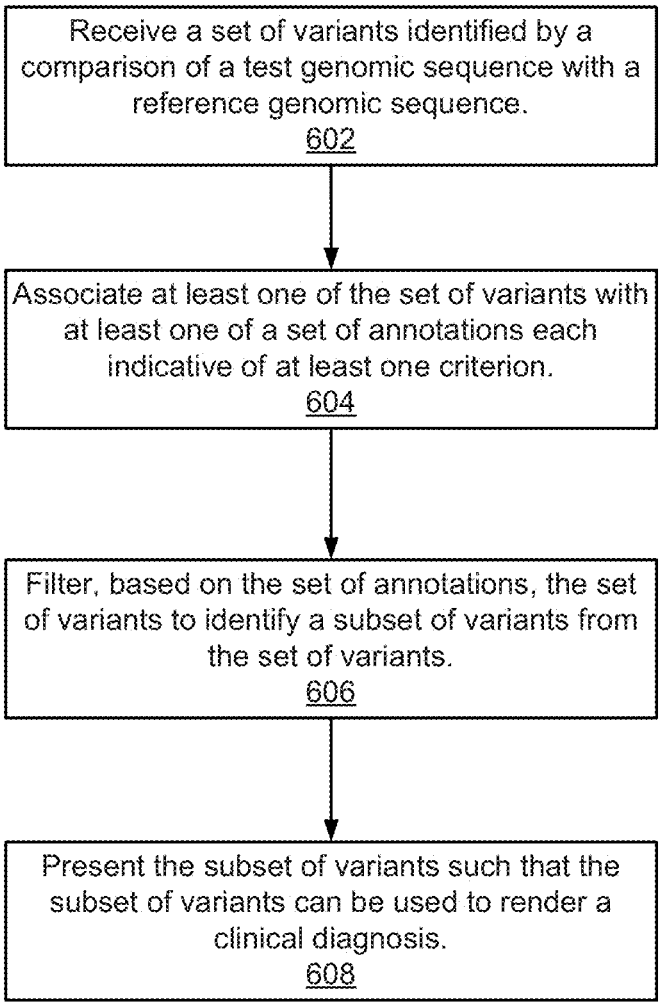
FIG. 8 is a flow chart illustrating a tertiary analysis phase method, according to an embodiment.

FIG. 8 is a flow chart illustrating a tertiary analysis phase method 600, according to an embodiment. In some embodiments, the tertiary analysis phase method 600 can be performed by a variant analysis system. The tertiary analysis phase method 600 includes receiving a set of variants identified by a comparison of a test DNA sequence with a reference DNA sequence, at 602. As discussed above, in some embodiments, the set of variants can be received in multiple different file formats and/or syntaxes. In such embodiments, the set of variants can be converted into a common file format and/or syntax that can be used in the remaining steps of method 600.

At least one of the set of variants is associated with at least one of a set of annotations each indicative of at least one criterion, at 604. As discussed above, in some embodiments, each variant can be annotated with data that can be used to determine a likelihood that that particular variant is associated with a disease, disorder and/or phenotype under analysis. Additionally, such annotations can be extracted from existing datasets and/or calculated using a variant analysis system.

The set of variants is filtered, based on the set of annotations, to identify a subset of variants from the set of variants, at 606. Each variant from the subset of variants is associated with at least one common annotation from the set of annotations. Such filtering can be based on any suitable criteria, such as, for example, the criteria described with respect to filter module 206 of FIG. 3. In some embodiments, a user (e.g., clinical geneticist or the like) provides the criteria to a variant analysis system performing method 600. In such embodiments, the user can search for and/or filter variants and/or genes associated with particular diseases and/or conditions. The subset of variants is then presented such that the subset of variants can be used to render a clinical diagnosis, at 608.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, while shown and described above (e.g., with respect to FIG. 2) as being implemented using a host device and a network, in other embodiments, a variant analysis system can be implemented locally. For example, the variant analysis system can be software stored in memory of a personal computing device (PC) and implemented by a processor of the PC. In such embodiments, for example, the PC can download the software from a host device and/or install the software using any suitable device such as a compact disc (CD).

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A non-transitory processor-readable medium storing code representing instructions to be executed by a processor, the code comprising code to cause the processor to:
   receive a plurality of variants identified by a comparison of a test DNA sequence with a reference DNA sequence;
   associate at least one variant from the plurality of variants with at least one annotation from a plurality of annotations including at least one of:
   (i) reported to cause a disorder and recognized to cause a disorder,
   (ii) unreported but expected to cause a disorder,
   (iii) unreported and of the type that might be causative of a disorder,
   (iv) unreported and unlikely to cause a disorder,
   (v) reported and recognized neutral variant, or
   (vi) unknown or not expected to be causative of disease, but associated with clinical presentation;
   filter, based on the plurality of annotations, the plurality of variants to identify a set of variants from the plurality of variants, each variant from the set of variants being associated with at least one common annotation from the plurality of annotations; and
   present the set of variants such that the set of variants can be used to render a clinical diagnosis.

2. The non-transitory processor-readable medium of claim 1, wherein the code includes code to cause the processor to filter for variants annotated as: having been reported to cause a disorder and recognized to cause a disorder.

3. The non-transitory processor-readable medium of claim 1, wherein the code includes code to cause the processor to filter for variants annotated as: unreported but expected to cause a disorder.

4. The non-transitory processor-readable medium of claim 1, wherein the code includes code to cause the processor to filter for variants annotated as: unreported and of the type that might be causative of a disorder.

5. The non-transitory processor-readable medium of claim 1, wherein the code includes code to cause the processor to filter for variants annotated as: unreported and unlikely to cause a disorder.

6. The non-transitory processor-readable medium of claim 1, wherein the code includes code to cause the processor to filter for variants annotated as: reported and recognized neutral variant.

7. The non-transitory processor-readable medium of claim 1, wherein the code includes code to cause the processor to filter for variants annotated as: unknown or not expected to be causative of disease, but having a known association with clinical presentation.

8. The non-transitory processor-readable medium of any one of claims 2 to 7, wherein variants are associated with annotations on the basis of a change in encoded amino acid, a change in an RNA processing site, or information from a human gene mutational database.

9. The non-transitory processor-readable medium of claim 8, wherein the variants involving a change in encoded amino acid include predictions of phenotype change.

10. The non-transitory processor-readable medium of claim 1, wherein the at least one variant is a single nucleotide polymorphism.

11. The non-transitory processor-readable medium of claim 1, wherein the at least one variant is a rare or infrequent allele.

12. The non-transitory processor-readable medium of claim 1, wherein the at least one variant is identified by genomic location, zygosity, allele frequency and/or SNP ID.

13. The non-transitory processor-readable medium of claim 1, wherein the code to cause the processor to receive includes code to cause the processor to receive the plurality of variants identified by the comparison of the test DNA sequence of at least 1 million base pairs with the reference DNA sequence of at least 1 million base pairs.

14. The non-transitory processor-readable medium of claim 1, wherein the code to cause the processor to receive includes code to cause the processor to receive the plurality of variants identified by the comparison of the test DNA sequence of at least 10 million base pairs with the reference DNA sequence of at least 10 million base pairs.

15. The non-transitory processor-readable medium of claim 1, wherein the code to cause the processor to receive includes code to cause the processor to receive the plurality of variants identified by the comparison of the test DNA sequence of at least 50 million base pairs with the reference DNA sequence of at least 50 million base pairs.

16. The non-transitory processor-readable medium of claim 1, wherein the code to cause the processor to receive includes code to cause the processor to receive the plurality of variants identified by the comparison of the test DNA sequence of an entire human genome with the reference DNA sequence of the entire human genome.

17. The non-transitory processor-readable medium of claim 1, wherein the code to cause the processor to receive includes code to cause the processor to receive the plurality of variants identified by the comparison of the test DNA sequence of a human exome with the reference DNA sequence of a human exome.

18. The non-transitory processor-readable medium of claim 1, wherein the test DNA sequence is a cDNA sequence, and/or is determined by clonal amplification of cDNA of an individual suspected of having a genetic disorder.

19. The non-transitory processor-readable medium of claim 1, wherein the code further comprises code to cause the processor to tag variants as: confirmed, preliminary, or sequence artifact.

20. The non-transitory processor-readable medium of claim 1, wherein the plurality of variants includes at least 1 million variants.

21. The non-transitory processor-readable medium of claim 1, wherein the plurality of variants includes at least 10 million variants.

22. The non-transitory processor-readable medium of claim 1, wherein the plurality of variants includes at least 15 million variants.

23. The non-transitory processor-readable medium of claim 1, wherein the code further comprises code to cause the processor to flag variants as benign, pathogenic, or unknown.

24. The non-transitory processor-readable medium of claim 23, wherein the code further comprises code to cause the processor to filter variants tagged as benign, pathogenic, or unknown.

25. The non-transitory processor-readable medium of claim 1, wherein the code includes code to cause the processor to filter variants in response to user inputs.

26. The non-transitory processor-readable medium of claim 19 or 23, wherein the code includes code to cause the processor to tag or flag variants in response to user inputs.

27. The non-transitory processor-readable medium of claim 1, wherein the plurality of variants is a first plurality of variants, the code to cause the processor to receive the first plurality of variants includes code to cause the processor to receive the first plurality of variants in a first syntax, the code to cause the processor to:
  receive, in a second syntax different from the first syntax, a second plurality of variants identified by a comparison of a third nucleotide sequence with the second nucleotide sequence;
  convert the first plurality of variants to a third syntax; and
  convert the second plurality of variants to the third syntax.

28. The non-transitory processor-readable medium of claim 1, wherein the code to cause the processor to associate includes code to cause the processor to associate the at least one variant from the plurality of variants with the at least one annotation from the plurality of annotations using a plurality of external databases.

29. A method for identifying a genetic disorder in an individual, comprising:
  determining a DNA sequence for a patient suspected of having a genetic disorder,
  comparing the DNA sequence with one or more reference sequences to identify a plurality of variants,
  annotating, at an annotation module implemented in at least one of a memory or a processing device, each variant from the plurality of variants with at least one annotation from a set of annotations including at least one of:
    (i) reported to cause a disorder and recognized to cause a disorder,
    (ii) unreported but expected to cause a disorder,
    (iii) unreported and of the type that might be causative of a disorder,
    (iv) unreported and unlikely to cause a disorder,
    (v) reported and recognized neutral variant, or
    (vi) unknown or not expected to be causative of disease, but associated with clinical presentation,
  filtering the plurality of variants on the basis of the set of annotations; and
  identifying the presence or absence of the genetic disorder.

30. The method of claim 29, wherein annotations from the set of annotations are assigned on the basis of a change in encoded amino acid, a change in an RNA processing site, or information from a human gene mutational database.

31. The method of claim 29, wherein the plurality of variants involving a change in encoded amino acid include predictions of phenotype change.

32. The method of claim 29, wherein at least one variant from the plurality of variants is a single nucleotide polymorphism.

33. The method of claim 29, wherein at least one variant from the plurality of variants is a rare or infrequent allele.

34. The method of claim 29, wherein the plurality of variants are identified by genomic location, zygosity, allele frequency and/or SNP ID.

35. The method of claim 29, wherein at least half of the individual's DNA sequence is determined.

36. The method of claim 29, wherein the DNA sequence of at least 1 million base pairs is determined.

37. The method of claim 29, wherein the DNA sequence of at least 10 million base pairs is determined.

38. The method of claim 29, wherein the DNA sequence of at least 50 million base pairs is determined.

39. The method of claim 29, wherein an exome sequence is determined.

40. The method of claim 29, wherein the DNA sequence is a cDNA sequence, and/or is determined by clonal amplification of cDNA.

41. The method of claim 29 further comprising, tagging the plurality of variants as confirmed, preliminary, or sequence artifact.

42. The method of claim 29, wherein the plurality of variants includes at least three million variants.

43. The method of claim 29, wherein the plurality of variants includes at least 10 million variants.

44. The method of claim 29, wherein the plurality of variants includes at least 15 million variants.

45. The method of claim 29, further comprising, flagging variants from the plurality of variants as benign, pathogenic, or unknown.

46. The method of claim 29, implemented using a non-transitory processor-readable medium.

* * * * *